(12) United States Patent
Browning et al.

(10) Patent No.: US 7,452,530 B2
(45) Date of Patent: Nov. 18, 2008

(54) REVERSAL OF VIRAL-INDUCED SYSTEMIC SHOCK AND RESPIRATORY DISTRESS BY BLOCKADE OF THE LYMPHOTOXIN BETA PATHWAY

(75) Inventors: Jeffrey L. Browning, Cambridge, MA (US); Maryann Puglielli, Atlanta, GA (US); Rafi Ahmed, Atlanta, GA (US)

(73) Assignees: Biogen Idec MA Inc., Cambridge, MA (US); Emory University, Atlanta, GA (US)

( * ) Notice: Subject to any disclaimer, the term of this patent is extended or adjusted under 35 U.S.C. 154(b) by 175 days.

(21) Appl. No.: 10/829,720

(22) Filed: Apr. 21, 2004

(65) Prior Publication Data

US 2004/0198635 A1 Oct. 7, 2004

Related U.S. Application Data

(63) Continuation of application No. 09/829,031, filed on Apr. 9, 2001, now abandoned, which is a continuation of application No. PCT/US99/23477, filed on Oct. 8, 1999.

(60) Provisional application No. 60/103,662, filed on Oct. 9, 1998.

(51) Int. Cl.
*A61K 38/19* (2006.01)
*A61K 38/01* (2006.01)
*A61K 39/395* (2006.01)
*A61K 39/44* (2006.01)
*A61K 45/00* (2006.01)
*A61K 41/00* (2006.01)
*A61K 47/00* (2006.01)
*A01N 63/00* (2006.01)

(52) U.S. Cl. .................. 424/93.2; 424/85.1; 424/93.21; 424/39.1

(58) Field of Classification Search ................ 424/85.1, 424/93.1
See application file for complete search history.

(56) References Cited

U.S. PATENT DOCUMENTS

| 3,773,919 | A | 11/1973 | Boswell et al. |
| 4,485,045 | A | 11/1984 | Regen |
| 4,544,545 | A | 10/1985 | Ryan et al. |
| 4,816,567 | A | 3/1989 | Cabilly et al. |

(Continued)

FOREIGN PATENT DOCUMENTS

DE 3218121 A1 11/1983

(Continued)

OTHER PUBLICATIONS

Fields et al. Virology 3rd edition, p. 1018 & p. 1169.*

(Continued)

*Primary Examiner*—Bruce Campell
*Assistant Examiner*—Bao Qun Li
(74) *Attorney, Agent, or Firm*—Lahive & Cockfield, LLP; Amy E. Mandragouras, Esq.; Cristin Howley Cowles

(57) ABSTRACT

This invention provides methods of inducing an antiviral response in an individual comprising administering to the individual an effective amount of a LT-B blocking agent and a pharmaceutically acceptable carrier. In particular this invention provides methods for treating viral-induced systemic shock and respiratory distress.

28 Claims, 7 Drawing Sheets

U.S. PATENT DOCUMENTS

| | | | |
|---|---|---|---|
| 5,225,538 | A | 7/1993 | Capon et al. |
| 5,661,004 | A | 8/1997 | Browning et al. |
| 5,670,149 | A | 9/1997 | Browning et al. |
| 5,795,964 | A | 8/1998 | Browning et al. |
| 5,925,351 | A | 7/1999 | Browning et al. |
| 6,312,691 | B1 | 11/2001 | Browning et al. |
| 6,403,087 | B1 | 6/2002 | Browning et al. |
| 6,669,941 | B1 | 12/2003 | Browning et al. |
| 7,001,598 | B2 | 2/2006 | Browning et al. |
| 7,030,080 | B2 | 4/2006 | Browning et al. |
| 7,060,667 | B1 | 6/2006 | Browning et al. |
| 7,255,854 | B1 | 8/2007 | Browning et al. |
| 7,309,492 | B2 | 12/2007 | Browning et al. |
| 2002/0039580 | A1 | 4/2002 | Browning et al. |
| 2005/0037003 | A1 | 2/2005 | Browning et al. |
| 2005/0281811 | A1 | 12/2005 | Browning et al. |
| 2006/0280722 | A1 | 10/2006 | Browning et al. |
| 2007/0116668 | A1 | 5/2007 | Browning et al. |

FOREIGN PATENT DOCUMENTS

| | | |
|---|---|---|
| EP | 0058481 B1 | 8/1982 |
| WO | WO-92/00329 A1 | 1/1992 |
| WO | WO-94/04679 A1 | 3/1994 |
| WO | WO-97/04658 A1 | 3/1994 |
| WO | WO-94/13808 A2 | 6/1994 |
| WO | WO-96/22788 A1 | 8/1996 |
| WO | WO-97/003687 A1 | 2/1997 |
| WO | WO 98/17313 A2 * | 4/1998 |
| WO | WO-98/18928 A1 | 5/1998 |

OTHER PUBLICATIONS

Sanchez et al. J. Virol. 2004, vol. 78, No. 9, pp. 10370-10377.*
Gupta et al. J. immunol. 2005, vol. 174, pp. 4198-4202.*
(Warfield et al. J. Immunol. 2005, vol. 175, pp. 1184-1191.*
Abe, Yashuhito et al, "Studies of Membrane-Associated and Soluble (Secreted) Lymphotoxin in Human Lymphokine-Activated T-Killer Cells in Vitro," *Lymphokine and Cytokine Research*, vol. 11(2):115-121 (1992).
Arulanadam, Antonio et al, "A Soluble Multimeric Recombinant CD2 Protein Identifies CD48 as a Low Affinity Ligand for Human CD2: Divergence of CD2 Ligands during the Evolution of Humans and Mice," *J. Exp. Med.*, vol. 177:1439-1450 (1993).
Bethell, Delia et al, " Pathophysiologic and Prognostic Role of Cytokines in Dengue Hemorrhagic Fever," *Journal of Infectious Diseases*, vol. 177:778-782 (1998).
Beutler, B. et al, "Passive Immunization Against Cachectin/Tumor Necrosis Factor Protects Mice from Lethal Effect of Endotoxin," *Science*, vol. 229:869-871 (1985).
Browning, Jeffrey et al, "Characterization of Surface Lymphotoxin Forms Use of Specific Monoclonal Antibodies and Soluble Recepetors," *Jour. of Immunology*, vol. 154:33-46 (1995).
Browning, Jeffrey et al, "Lymphotoxin Beta, a Novel Member of the TNF Family that Forms a Hetermeric Complex with Lymphotoxin on the Cell Surface," *Cell*, vol. 72:847-856 (1993).
Chaplin, D. et al, "Cytokine regulation of secondary lymphoid organ development," *Curr. Opin. in Immunology*, vol. 10:289-297 (1998).
Crowe, Paul et al, "Production of lymphotoxin (LT-Alpha) and a soluble dimeric form of its receptor using the baculovirus expression system," *Jour. of Immunological Methods*, vol. 168:79-89 (1994).
Crowe, Paul et al, " A Lymphotoxin-beta-Specific Receptor," *Science*, vol. 264:707-710 (1994).
Duzgunes et al, "Liposome Targeting to HIV-Infected Cells via Recombinant Soluble CD4 and CD4-IgG Immunoadhesin," *Journal of Cell. Biochem.*, Suppl. 16E:77 (1992).
Eppstein, Deborah et al, "Biological activity of a liposome-encapsulated murine interferon gamma is mediated by a cell membrane receptor," *Proc. Nat'l. Acad. Sci. USA*, vol. 82:3688-3692 (1995).
Fagerstam, Lars et al, "Surface Plasmon Resonance Detection in Affinity Technologies," *Handbook of Affinity Chromatography*, Marcel Dekker, Inc., N.Y., pp. 229-252 (1993).
Force, Walker et al, "Mouse Lymphotoxin-beta Receptor Molecular Genetics, Ligand Binding, and Expression," *Journal of Immunology*, vol. 155:5280-5288 (1995).
Hober, Didier et al, "Serum Levels of Tumor Necrosis Factor-alpha (TNF-alpha), INterleukin-6 (IL-6), and interleukin-1 beta (IL-1 beta) in Dengue-Infected Patients," *Am. Jour. Trop. Med. Hyg.*, vol. 48(3):324-331 (1993).
Hwang, Karl et al, "Hepatic uptake and degradation if unilamellar sphingomyelin/cholesterol liposomes: a kinetic study," *Proc. Nat'l. Acad. Sci. USA*, vol. 77(7):4030-0434 (1980).
Lacy, Mark et al, "Viral Hemorrhagic Fevers," *Adv. in Pediatric Infectious Diseases*, vol. 12:21-53 (1997).
Lane, Peter et al, "Activated human T cells express a ligand for the human B cell-associated antigen CD40 which participates in T cell-dependent activation of B lymphocytes," *Eur. Journal of Immunology*, vol. 22:2573-2578 (1992).
Langer, Robert, "Controlled release of macromolecules," *Chemtech*, vol. 12:98-105 (1982).
Langer, Robert et al, "Biocompatibility of polymeric delivery systems for macromolecules," *Jour of Biomedical Materials Research*, vol. 15:267-277 (1981).
Mackay, Fabienne et al, "Cytotoxic Activities of Recombinant Soluble Murine Lymphotoxin-alpha and Lymphotoxin-alpha/beta Complexes," *Jour. of Immunology*, vol. 159:3299-3310 (1997).
Mauri, Davide et al, "Light, a New Member of the TNF Superfamily, and Lymphotoxin alpha are Ligands for Herpesvirus Entry Mediator," *Immunity*, vol. 8:21-30 (1998).
Miller, Glenn et al, "Specific Interaction of lymphocyte Function-associated Antigen 3 with CD2 can Inhibit T Cell Responses," *Jour. Experimental Medicine*, vol. 178:211-222 (1993).
Montgomery, Rebecca et al, "Herpes Simplex Virus-1 Entry into Cells Mediated by a Novel Member of the TNF/NGF Recpetor Family," *Cell*, vol. 87:427-436 (1996).
Morrison, Sherie, "In Vitro Antibodies: Strategies for Production and Application," *Annal Review of Immunology*, vol. 10:239-265 (1992).
Morrison, Sherie et al, "Chimeric human antibody molecules: Mouse antigen-binding domains with human constant region domains," *Proc. Nat'l Academy of Sciences USA*, vol. 81:6851-6855 (1984).
Pass, Harvey et al, "The Macrophage, TNF, and other Cytokines," *Chest Surgery Clinics of North America*, vol. 5(1):73-90 (1995).
Queen, Cary et al, "A humanized antibody that binds to the interleukin 2 recpetor," *Proc. Natl'l. Acad. Sci. USA*, vol. 86:10029-10033 (1989).
Roitt et al, Immunology, 3rd ed., pp. 4.8 (1993).
Sheehan, Kathleen et al, "Generation and Characterization of Hamster Monoclonal Antibodies that Neutralize Murine Tumor Necrosis Factors," *Jour. of Immunology*, vol. 142(11):3884-3894 (1989).
Sidman, Kenneth et al, "Controlled Release of Macromolecules and Pharmaceuticals from Synthetic Polypeptides Based on Glutamic Acid," *Biopolymers*, vol. 22:547-556 (1983).
Smith, Craig et al, "The TNF Receptor Superfamily of Cellular and Viral Proteins: Activation, Costimulation, and Death," *Cell*, vol. 76:959-962 (1994).
Traunecker, Andre et al, "Highly efficient neutralization of HIV with recombinant CD4-immunoglobulin molecules," *Nature*, vol. 339:68-70 (1989).
Winter, Greg et al, "Man-made antibodies," *Nature*, vol. 349:293-299 (1991).
Wong, Grace et al, "Tumour necrosis factors alpha and beta inhibit virus replication and synergize with interferons," *Nature*, vol. 323:819-822 (1986).
Zhou, M. et al, "Real-Time Measurements of Kinetics of EGF Binding to Soluble EGF Receptor Monomers and Dimers Support the Dimerization Model for Receptor Activation," *Biochemistry*, vol. 32:8193-8198 (1993).
Nicola, Anthony V. et al., "Monoclonal Antibodies to Distinct Sites on Herpes Simplex Virus (HSV) Glycoprotein D Block HSV Binding to HVEM," *Journal of Virology*, vol. 72(5):3595-3601 (1998).

* cited by examiner

REVERSAL OF VIRAL-INDUCED SYSTEMIC SHOCK AND RESPIRATORY DISTRESS BY BLOCKADE OF THE LYMPHOTOXIN BETA PATHWAY

RELATED APPLICATIONS

This is a continuation of U.S. patent application Ser. No. 09/829,031, filed on Apr. 9, 2001, which is a continuation of PCT/US99/23477, filed on Oct. 8, 1999 as a continuation-in-part of prior U.S. Provisional Ser. No. 60/103,662 filed Oct. 9, 1998. The teachings of the earlier-filed Provisional patent application are incorporated herein by reference.

FIELD OF THE INVENTION

This invention relates generally to methods of inducing an antiviral response in an individual. In particular, this invention provides methods for treating viral-induced systemic shock and respiratory distress in an individual. The methods involves administration of certain "lymphotoxin-beta blocking agents".

BACKGROUND OF THE INVENTION

Several viruses including Sin Nombre (SNV), Ebola, Marburg, Lassa, and Dengue all cause acute diseases with many of the following symptoms: rapid onset, fever, systemic shock, and pulmonary distress (Lacy et al (1997) Adv. Ped. Inf. Dis. 12:21). Another commonality among these infections is the systemic distribution of viral infection, targeting endothelial cells and macrophages (Lacy et al. (1997) Adv. Ped. In. Dis. 12:21). Most of these emerging viruses, with the exception of SNV, were initially identified decades ago. In the years since their discovery these pathogens have re-emerged in outbreaks worldwide. As of June 1998 there have been 183 confirmed cases of SNV, the causative agent of Hantavirus Pulmonary Shock Syndrome, in the southwestern United States due to an increase in deer mouse populations. Only 55% of these cases have survived infection (Centers for Disease Control and Prevention. MMWR. 47, 449 (1998)). Little is currently known about the pathogenesis of these viruses nor how to effectively treat the thousands of patients infected globally each year suffering from viral-induced systemic shock and respiratory distress.

Thus, there exists a need to identify novel methods for treating viral-induced systemic shock and respiratory distress in an individual.

SUMMARY OF THE INVENTION

The present invention solves the problem referred to above by providing pharmaceutical compositions and methods for treating viral-induced systemic shock and respiratory distress in an individual.

The methods and compositions of this invention capitalize in part on the discovery that certain agents, defined herein as lymphotoxin-beta (LT-B) blocking agents may be used in treating viral-induced systemic shock and respiratory distress in an individual. In one embodiment, the LT-B blocking agent is a lymphotoxin-beta receptor (LT-B-R) blocking agent. In a preferred embodiment, the LT-B-R blocking agent is an antibody against a lymphotoxin-B receptor or a soluble lymphotoxin B receptor. In a most preferred embodiment, the LT-B-R blocking agent is a recombinant LT-B-R fusion protein that has an LT-B-R extracellular ligand binding domain fused to an immunoglobulin constant heavy chain domain.

The foregoing and other objects, features, aspects and advantages of the present invention, as well as the invention itself, will be more fully understood from the following description of preferred embodiments.

DETAILED DESCRIPTION OF THE INVENTION

Definitions

Figure 1:
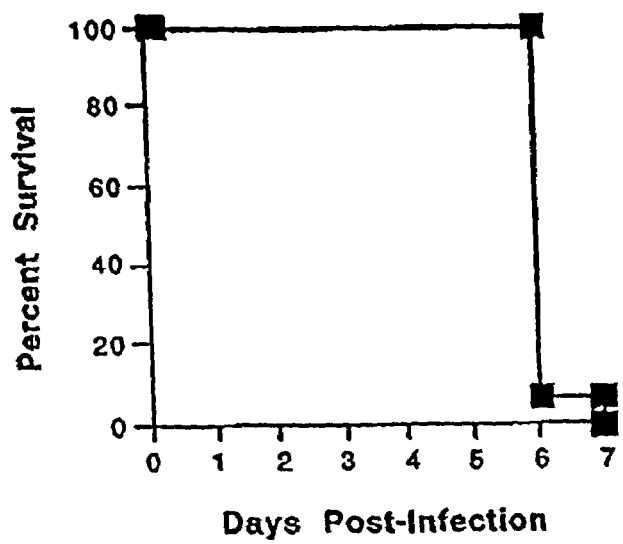
FIG. 1 shows that infection of NZB mice with Clone 13 LCMV results in mortality. Mortality curve of NZB mice infected with LCMV-13 (n=14) and viral titers in various tissues of LCMV-13 (n=7) infected mice six days post-infection.
Figure 1:
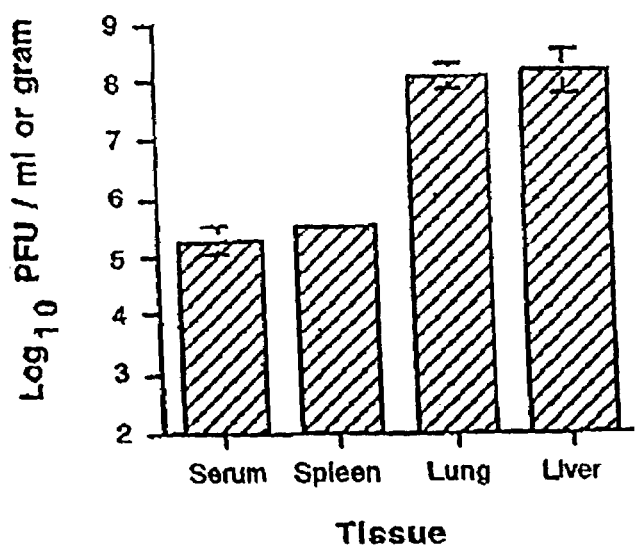
Figure 2A:
FIG. 2 shows the histological profile of LCMV-13 infection in NZB mice. (A) Normal lung at (100×, H+E) (B) Interstitial pneumonitis with mononuclear cell infiltrate and alveolar wall thickening in the lung, day 5 post-infection (100×, H+E) (C) Lymphoid depletion, cellular necrosis and obliteration of follicular architecture in the spleen (25×, H+E) (D) Higher magnification showing cellular necrosis and karyorrhectic debris in the spleen (158, H+E) (E) LCMV-13 positive endothelial cells (arrows) and macrophages (white arrows) in the lung (100×, IHC) (F) LCMV-13 positive endothelial cells endothelial cells (arrows) and mesothelial cells (arrow heads), and macrophages (white arrows) in the spleen (50×, IHC) (G) LCMV-13 positive endothelial cells in the heart (100×, IHC) (H) LCMV-13 positive Kupffer cells and sinusoidal lining cells in the liver (100×, IHC).
Figure 2B:
Figure 2C:
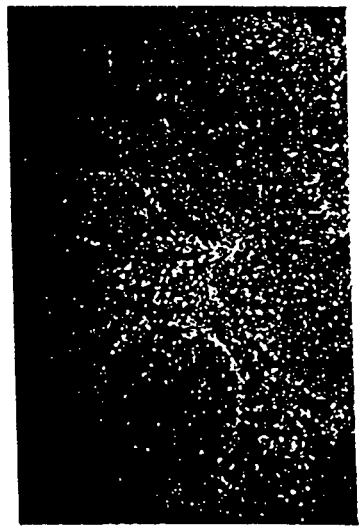
Figure 2D:
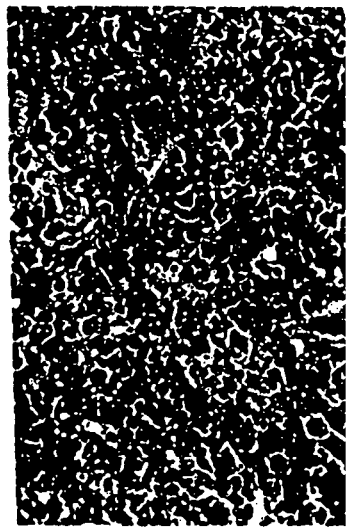
Figure 2F:
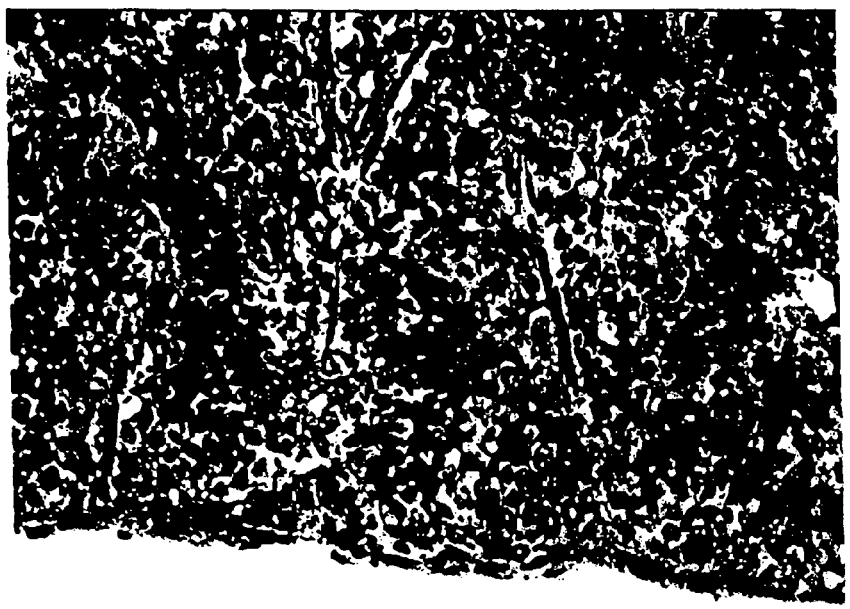
Figure 2E:
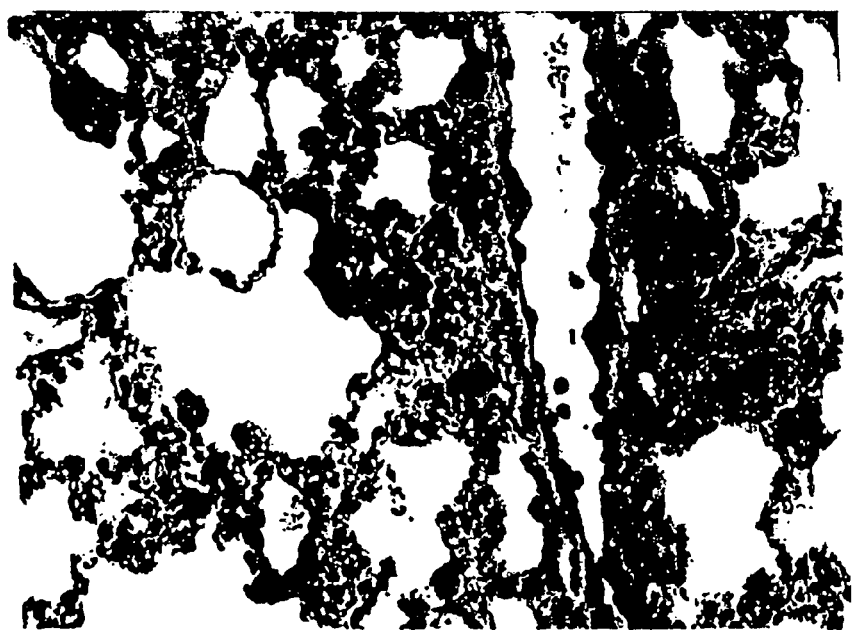
Figure 2G:
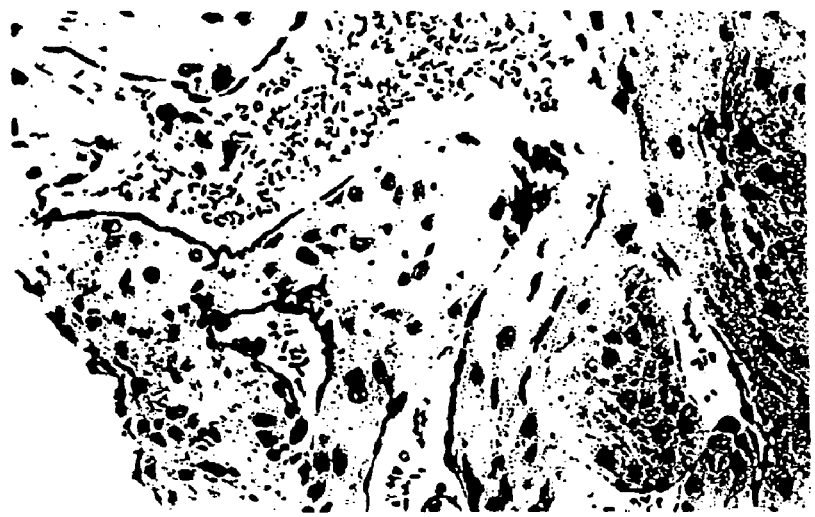
Figure 2H:
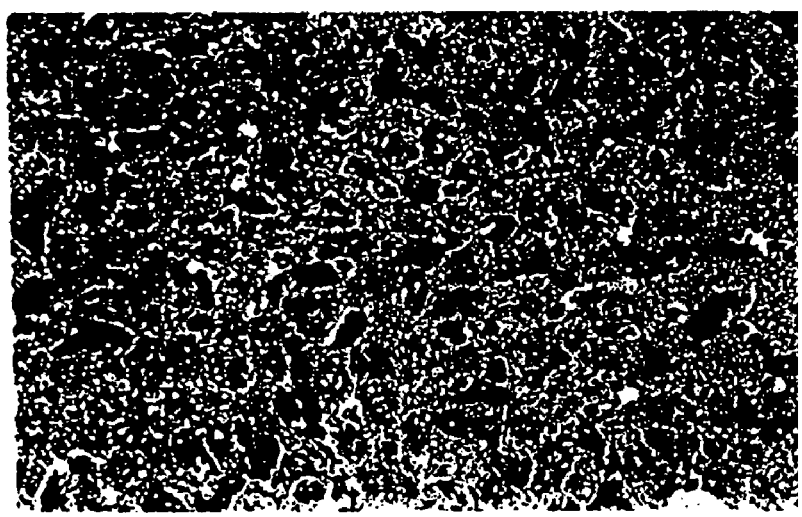

In order to more clearly and concisely point out the subject matter of the claimed invention, the following definitions are provided for specific terms used in the following written description and appended claims.

Lymphotoxin-beta (LT-beta) is a member of the TNF family of ligands, which also includes the ligands to the Fas, CD27, CD30, CD40, OX-40 and 4-1BB receptors (Smith et al., Cell, 76, pp. 959-62 (1994)). Signaling by several members of the TNF family-including TNF, LT-alpha, LT-beta and Fas-can induce tumor cell death by necrosis or apoptosis (programmed cell death). In non-tumorigenic cells, TNF and many of the TNF family ligand-receptor interactions influence immune system development and responses to various immune challenges.

Lymphotoxin-beta (also called p33), has been identified on the surface of T lymphocytes, T cell lines, B cell lines and lymphokine-activated killer (LAK) cells. LT-beta is the subject of applicants' co-pending international applications PCT/US91/04588, published Jan. 9, 1992 as WO 92/00329; and PCT/US93/11669, published Jun. 23, 1994 as WO 94/13808, which are herein incorporated by reference.

The LT- beta receptor, a member of the TNF family of receptors, specifically binds to surface LT ligands. LT-beta-R binds LT heteromeric complexes (predominantly LT-alpha 1/beta 2 and LT-alpha 2/beta 1) but does not bind TNF or LT-alpha (Crowe et al., Science, 264, pp. 707-10 (1994)). Signaling by LT-beta-R may play a role in peripheral lymphoid organ development and in humoral immune responses.

LT-beta-R mRNAs are found in human spleen, thymus and other major organs. LT-beta-R expression patterns are similar to those reported for p55-TNF-R except that LT-beta-R is lacking on peripheral blood T cells and T cell lines.

The term "LT-beta-blocking agent" refers to an agent that can diminish ligand binding to LT-beta, cell surface LT-beta clustering or LT-beta signalling, or that can influence how the LT-beta signal is interpreted within the cell. Examples of LT-beta-blocking agents include anti-LT-beta, soluble LT-beta-R-Fc molecules, and anti-LT-alpha, anti-LT-alpha/beta and anti-LT-beta-R Abs. Preferably, the antibodies do not cross-react with the secreted form of LT-alpha .

The term "LT-beta-receptor blocking agent" refers to an agent that can diminish ligand binding to LT-beta-R, cell surface LT-beta-R clustering or LT-beta-R signalling, or that can influence how the LT-beta-R signal is interpreted within the cell. Examples of LT-beta-R blocking agents include soluble LT-beta-R-Fc molecules, and and anti-LT-beta-R Abs. Preferably, the antibodies do not cross-react with the secreted form of LT-alpha.

The term "anti-LT-beta receptor antibody" refers to any antibody that specifically binds to at least one epitope of the LT-beta receptor.

The term "anti-LT antibody" refers to any antibody that specifically binds to at least one epitope of LT-alpha, LT-beta or a LT-alpha/beta complex.

The term "LT ligand" refers to a LT heteromeric complex or derivative thereof that can specifically bind to the LT-beta receptor.

The term "LT-beta-R signaling" refers to molecular reactions associated with the LT-beta-R pathway and subsequent molecular reactions which result therefrom.

The term "LT-beta-R ligand binding domain" refers to the portion or portions of the LT-beta-R that are involved in specific recognition of and interaction with a LT ligand.

The terms "LT-alpha/beta heteromeric complex" and "LT heteromeric complex" refer to a stable association between at least one LT-alpha and one or more LT-beta subunits, including soluble, mutant, altered and chimeric forms of one or more of the subunits. The subunits can associate through electrostatic, van der Waals, or covalent interactions. Preferably, the LT-alpha/62 heteromeric complex has at least two adjacent LT-beta subunits and lacks adjacent LT-alpha subunits. When the LT-alpha/beta heteromeric complex serves as a LT-beta-R activating agent in a cell growth assay, the complex is preferably soluble and has the stoichiometry LT-alpha 1/beta 2.

Soluble LT-alpha/62 heteromeric complexes lack a transmembrane domain and can be secreted by an appropriate host cell which has been engineered to express LT-alpha and/or LT-beta subunits (Crowe et al., J. Immunol. Methods, 168, pp. 79-89 (1994)).

The terms "surface LT-alpha/62 complex" and "surface LT complex" refer to a complex comprising LT-alpha and membrane-bound LT-beta subunits-including mutant, altered and chimeric forms of one or more of the subunits-which is displayed on the cell surface. "Surface LT ligand" refers to a surface LT complex or derivative thereof that can specifically bind to the LT-beta receptor.

An "effective amount" is an amount sufficient to effect beneficial or desired clinical results. An effective amount can be administered in one or more administrations. For purposes of this invention, an effective amount of an agent which blocks the binding of lymphotoxin-B to its receptor is an amount of the agent that is sufficient to ameliorate, stabilize, or delay the development of a viral response. In particular, an agent that is sufficient to ameliorate, stabilize, or delay the development of viral-induced systemic shock and respiratory distress. Detection and measurement of these indicators of efficacy are known to those of skill in the art.

An "individual" refers to vertebrates, particularly members of a mammalian species, and includes but is not limited to domestic animals, sports animals, and primates, including humans.

"functional equivalent" of an amino acid residue is (i) an amino acid having similar reactive properties as the amino acid residue that was replaced by the functional equivalent; (ii) an amino acid of an antagonist of the invention, the amino acid having similar properties as the amino acid residue that was replaced by the functional equivalent; (iii) a non-amino acid molecule having similar properties as the amino acid residue that was replaced by the functional equivalent.

A first polynucleotide encoding a proteinaceous antagonist of the invention is "functionally equivalent" compared with a second polynucleotide encoding the antagonist protein if it satisfies at least one of the following conditions:

(a): the "functional equivalent" is a first polynucleotide that hybridizes to the second polynucleotide under standard hybridization conditions and/or is degenerate to the first polynucleotide sequence. Most preferably, it encodes a mutant protein having the activity of an integrin antagonist protein;

(b) the "functional equivalent" is a first polynucleotide that codes on expression for an amino acid sequence encoded by the second polynucleotide.

"functional equivalent" of an amino acid residue is (i) an amino acid having similar reactive properties as the amino acid residue that was replaced by the functional equivalent; (ii) an amino acid of an antagonist of the invention, the amino acid having similar properties as the amino acid residue that was replaced by the functional equivalent; (iii) a non-amino acid molecule having similar properties as the amino acid residue that was replaced by the functional equivalent.

A first polynucleotide encoding a proteinaceous antagonist of the invention is "functionally equivalent" compared with a second polynucleotide encoding the antagonist protein if it satisfies at least one of the following conditions:

(a): the "functional equivalent" is a first polynucleotide that hybridizes to the second polynucleotide under standard hybridization conditions and/or is degenerate to the first polynucleotide sequence. Most preferably, it encodes a mutant protein having the activity of an integrin antagonist protein;

(b) the "functional equivalent" is a first polynucleotide that codes on expression for an amino acid sequence encoded by the second polynucleotide.

The LT-B blocking agents used in the invention include, but are not limited to, the agents listed herein as well as their functional equivalents. As used herein, the term "functional equivalent" therefore refers to a LT-B blocking agent or a polynucleotide encoding the LT-B blocking agent that has the same or an improved beneficial effect on the recipient as the LT-B blocking agent of which it is deemed a functional equivalent. As will be appreciated by one of ordinary skill in the art, a functionally equivalent protein can be produced by recombinant techniques, e.g., by expressing a "functionally equivalent DNA". Accordingly, the instant invention embraces LT-B blocking agent encoded by naturally-occurring DNAs, as well as by non-naturally-occurring DNAs which encode the same protein as encoded by the naturally-occurring DNA. Due to the degeneracy of the nucleotide coding sequences, other polynucleotides may be used to encode LT-B blocking agents. These include all, or portions of the above sequences which are altered by the substitution of different codons that encode the same amino acid residue within the sequence, thus producing a silent change. Such altered sequences are regarded as equivalents of these sequences. For example, Phe (F) is coded for by two codons, TTC or TTT, Tyr (Y) is coded for by TAC or TAT and His (H) is coded for by CAC or CAT. On the other hand, Trp (W) is coded for by a single codon, TGG. Accordingly, it will be appreciated that for a given DNA sequence encoding a particular integrin there will be many DNA degenerate sequences that will code for it. These degenerate DNA sequences are considered within the scope of this invention.

The term "fusion" or "fusion protein" refers to a co-linear, covalent linkage of two or more proteins or fragments thereof via their individual peptide backbones, most preferably through genetic expression of a polynucleotide molecule encoding those proteins. It is preferred that the proteins or fragments thereof are from different sources so that this type of fusion protein is called a "chimeric" molecule. Thus, preferred fusion proteins are chimeric proteins that include a LT-B blocking agent or fragment covalently linked to a second moiety that is not a LT-B blocking agent. Preferred fusion proteins of the invention may include portions of intact antibodies that retain antigen-binding specificity, for example, Fab fragments, Fab' fragments, F(ab')2 fragments, F(v) fragments, heavy chain monomers or dimers, light chain monomers or dimers, dimers consisting of one heavy and one light chain, and the like.

The most preferred fusion proteins are chimeric and comprise a LT-B blocking agent moiety fused or otherwise linked to all or part of the hinge and constant regions of an immunoglobulin light chain, heavy chain, or both. Thus, this invention features a molecule which includes: (1) a LT-B blocking agent moiety, (2) a second peptide, e.g., one which increases solubility or in vivo life time of the LT-B blocking agent moiety, e.g., a member of the immunoglobulin super family or fragment or portion thereof, e.g., a portion or a fragment of IgG, e.g., the human IgGl heavy chain constant region, e.g., CH2, CH3, and hinge regions. Specifically, a "LT-B or LT-B-R/Ig fusion" is a protein comprising a biologically active LT-B blocking of the invention (e.g. a soluble LT-B-R, or a biologically active fragment thereof linked to an N-terminus of an immunoglobulin chain wherein a portion of the N-terminus of the immunoglobulin is replaced with the LT-B blocking agent. A species of LT-B or LT-B-R/Ig fusion is an "LT-B-R/Fc fusion" which is a protein comprising an LT-B-R of the invention linked to at least a part of the constant domain of an immunoglobulin. A preferred Fc fusion comprises a LT-B blocking agent of the invention linked to a fragment of an antibody containing the C terminal domain of the heavy immunoglobulin chains.

"standard hybridization conditions"—salt and temperature conditions substantially equivalent to 0.5×SSC to about 5×SSC and 65° C. for both hybridization and wash. The term "standard hybridization conditions" as used herein is therefore an operational definition and encompasses a range of hybridization conditions. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulfate, and 100 μg/ml denatured, sonicated salmon sperm DNA at 65° C. for 12-20 hours, and washing with 75 mM NaCl/7.5 mM sodium citrate (0.5×SSC)/1% SDS at 65° C. Lower stringency conditions may, for example, include hybridizing with plaque screen buffer, 10% dextran sulfate and 110 μg/ml denatured, sonicated salmon sperm DNA at 55° C. for 12-20 hours, and washing with 300 mM NaCl/30 mM sodium citrate (2.0×SSC)/1% SDS at 55° C. See also *Current Protocols in Molecular Biology*, John Wiley & Sons, Inc. New York, Sections 6.3.1-6.3.6, (1989).

A "therapeutic composition" as used herein is defined as comprising the proteins of the invention and other biologically compatible ingredients. The therapeutic composition may contain excipients such as water, minerals and carriers such as protein.

II. Description of the Preferred Embodiments

The present invention depends in part upon the discovery that LT-B blocking agents can induce an antiviral response in an individual. It was found that treating an individual infected with a virus can greatly increase the survival rate of the individual. Specifically, it was shown that treating LCMV-13 infected NZB mice with a LT-B blocking agent, such as LTβR-Ig fusion protein increased their survival rate 73%.

Currently treatment for Ebola, Dengue, SNV and other viruses mentioned herein is preventative via education on transmission of disease. Vaccines do not exist for these highly pathogenic viruses. Ribavirin, a guanidine analog, has been employed as a generic antiviral drug to several of these infections with reproducible success only documented in treatment of Lassa Fever when used early on in the illness (M. D. Lacy and R. A. Smego, *Adv. Ped. Inf Dis.*, 12, 21 (1997). Our data indicate that some of the pathology associated with these viruses may be immune mediated. Blockade of the LT system could greatly increase the chance for survival by transiently reducing virus specific CD8 T cells numbers and their functionality. Clinical trials that employ several means of blocking the TNFα pathway are already underway for the treatment of several ailments (H. I. Pass, D. Mew, H. A. Pass, et al., *Chest Surg. Clin. N. Amer.* 5, 73 (1995). We believe the LTβR-Ig treatment should be considered for further testing in animal models for eventual use in human trials involving patients with acute, rapidly progressive viral infections involving shock and/or pulmonary distress.

LT-B Blocking Agents

In one embodiment of this invention, the LT-beta blocking agent comprises an antibody (Ab) directed against LT-beta that inhibits LT-beta signaling. Preferably, the anti-LT-beta Ab is a monoclonal antibody (mAb). Inhibitory anti-LT-beta Abs and other LT-beta blocking agents can be identified using screening methods that detect the ability of one or more agents to bind to a LT ligand, or to inhibit the effects of LT-beta signalling on cells.

In another embodiment of this invention, the LT-beta blocking agent comprises an LT-beta receptor (LT-B-R) blocking agent. In a preferred embodiment, the LT-B-R blocking agent is an antibody (Ab) directed against LT-beta-R that inhibits LT-beta-R signaling. Preferably, the anti-LT-beta-R Ab is a monoclonal antibody (mAb). One such inhibitory anti-LT-beta-R mAb is BDA8 mAb. Inhibitory anti-LT-beta-R Abs and other LT-beta-R blocking agents can be identified using screening methods that detect the ability of one or more agents either to bind to the LT-beta-R or LT ligand, or to inhibit the effects of LT-beta-R signalling on cells.

One screening method makes use of the cytotoxic effects of LT-beta-R signalling on tumor cells bearing the LT-beta-R. Tumor cells are exposed to one or more LT-beta-R activating agents to induce LT-beta-R signalling. LT-beta-R activating agents include LT-alpha/62 heteromeric complexes (preferably soluble LT-alpha 1/beta 2) in the presence of IFN-gamma, or an activating anti-LT-beta-R Ab (see below; also described in applicants' co-pending U.S. application Ser. No. 08/378,968).

Antibodies and other agents that can block LT-beta-R signalling are selected based on their ability to inhibit the cytotoxic effect of LT-beta-R signalling on tumor cells in the following assay:
1) Tumor cells such as HT29 cells are cultured for three to four days in a series of tissue culture wells containing media and at least one LT-beta-R activating agent in the presence or absence of serial dilutions of the agent being tested;
2) A vital dye stain which measures mitochondrial function such as MTT is added to the tumor cell mixture and reacted for several hours;
3) The optical density of the mixture in each well is quantitated at 550 nm wavelength light (OD 550). The OD 550 is proportional to the number of tumor cells remaining in the presence of the LT-beta-R activating agent and the test LT-beta-R blocking agent in each well. An agent or combination of agents that can reduce LT-beta-R-activated tumor cell cytotoxicity by at least 20% in this assay is a LT-beta-R blocking agent within the scope of this invention.

Any agent or combination of agents that activate LT-beta-R signalling can be used in the above assay to identify LT-beta-R blocking agents. LT-beta-R activating agents that induce LT-beta-R signalling (such as activating anti-LT-beta-R mAbs) can be selected based on their ability-alone or in combination with other agents-to potentiate tumor cell cytotoxicity using the tumor cell assay described above.

Another method for selecting an LT-beta-R blocking agent is to monitor the ability of the putative agent to directly interfere with LT ligand-receptor binding. An agent or combination of agents that can block ligand-receptor binding by at least 20% is an LT-beta-R blocking agent within the scope of this invention.

Any of a number of assays that measure the strength of ligand-receptor binding can be used to perform competition assays with putative LT-beta-R blocking agents. The strength of the binding between a receptor and ligand can be measured using an enzyme-linked immunoadsorption assay (ELISA) or a radio-immunoassay (RIA). Specific binding may also be measured by fluorescently labelling antibody-antigen complexes and performing fluorescence-activated cell sorting (FACS) analysis, or by performing other such immunodetection methods, all of which are techniques well known in the art.

The ligand-receptor binding interaction may also be measured with the BIAcore TM instrument (Pharmacia Biosensor) which exploits plasmon resonance detection (Zhou et al., Biochemistry, 32, pp. 8193-98 (1993); Faegerstram and O'Shannessy, "Surface plasmon resonance detection in affinity technologies", in Handbook of Affinity Chromatography, pp. 229-52, Marcel Dekker, Inc., New York (1993)).

The BIAcore™ technology allows one to bind receptor to a gold surface and to flow ligand over it. Plasmon resonance detection gives direct quantitation of the amount of mass bound to the surface in real time. This technique yields both on and off rate constants and thus a ligand-receptor dissociation constant and affinity constant can be directly determined in the presence and absence of the putative LT-beta-R blocking agent.

With any of these or other techniques for measuring receptor-ligand interactions, one can evaluate the ability of a LT-beta-R blocking agent, alone or in combination with other agents, to inhibit binding of surface or soluble LT ligands to surface or soluble LT-beta-R molecules. Such assays may also be used to test LT-beta-R blocking agents or derivatives of such agents (e.g. fusions, chimeras, mutants, and chemically altered forms)-alone or in combination—to optimize the ability of that altered agent to block LT-beta-R activation.

The LT-beta-R blocking agents in one embodiment of this invention comprise soluble LT-beta receptor molecules. The sequence of the extracellular portion of the human LT-beta-R, which encodes the ligand binding domain is shown in FIG.1 of U.S. Pat. No. 5,925,351, incorporated by reference herein. Using the sequence information in FIG. 1 of U.S. Pat. No. 5,925,351 and recombinant DNA techniques well known in the art, functional fragments encoding the LT-beta-R ligand binding domain can be cloned into a vector and expressed in an appropriate host to produce a soluble LT-beta-R molecule. Soluble LT-beta-R molecules that can compete with native LT-beta receptors for LT ligand binding according to the assays described herein are selected as LT-beta-R blocking agents.

A soluble LT-beta receptor comprising amino acid sequences selected from those shown in FIG. 1 of U.S. Pat. No. 5,925,351 may be attached to one or more heterologous protein domains ("fusion domain") to increase the in vivo stability of the receptor fusion protein, or to modulate its biological activity or localization. Preferably, stable plasma proteins-which typically have a half-life greater than 20 hours in the circulation-are used to construct the receptor fusion proteins. Such plasma proteins include but are not limited to: immunoglobulins, serum albumin, lipoproteins, apolipoproteins and transferrin. Sequences that can target the soluble LT-beta-R molecule to a particular cell or tissue type may also be attached to the LT-beta-R ligand binding domain to create a specifically-localized soluble LT-beta-R fusion protein. All or a functional portion of the LT-beta-R extracellular region (FIG. 1 of U.S. Pat. No. 5,925,351) comprising the LT-beta-R ligand binding domain may be fused to an immunoglobulin constant region like the Fc domain of a human IgG1 heavy chain (Browning et al., J. Immunol., 154, pp. 33-46 (1995)). Soluble receptor-IgG fusion proteins are common immunological reagents and methods for their construction are known in the art (see e.g., U.S. Pat. No. 5,225,538). A functional LT-beta-R ligand binding domain may be fused to an immunoglobulin (Ig) Fc domain derived from an immunoglobulin class or subclass other than IgG1. The Fc domains of antibodies belonging to different Ig classes or subclasses can activate diverse secondary effector functions. Activation occurs when the Fc domain is bound by a cognate Fc receptor. Secondary effector functions include the ability to activate the complement system, to cross the placenta, and to bind various microbial proteins. The properties of the different classes and subclasses of immunoglobulins are described in Roitt et al., Immunology, p. 4.8 (Mosby—Year Book Europe Ltd., 3d ed. 1993). The complement enzyme cascade can be activated by the Fc domains of antigen-bound IgG1, IgG3 and IgM antibodies. The Fc domain of IgG2 appears to be less effective, and the Fc domains of IgG4, IgA, IgD and IgE are ineffective at activating complement. Thus one can select a Fc domain based on whether its associated secondary effector functions are desirable for the particular immune response or disease being treated with the LT-beta-R-Fc fusion protein. If it would be advantageous to harm or kill the LT ligand-bearing target cell, one could select an especially active Fc domain (IgG1) to make the LT-beta-R-Fc fusion protein. Alternatively, if it would be desirable to target the LT-beta-R-Fc fusion to a cell without triggering the complement system, an inactive IgG4 Fc domain could be selected.

Mutations in Fc domains that reduce or eliminate binding to Fc receptors and complement activation have been described (S. Morrison, Annu. Rev. Immunol., 10, pp. 239-65 (1992)). These or other mutations can be used, alone or in combination, to optimize the activity of the Fc domain used to construct the LT-beta-R-Fc fusion protein.

The production of a soluble human LT-beta-R fusion protein comprising ligand binding sequences fused to a human immunoglobulin Fc domain (hLT-beta-R-Fc) is described in Example 1 of U.S. Pat. No. 5,925,351 incorporated by reference herein. One CHO line made according to Example 1 that secretes hLT-beta-R-Fc is called "hLT beta; R-hG1 CHO#14". A sample of this line was deposited on Jul. 21, 1995 with the American Type Culture Collection (ATCC) (Rockville, Md.) according to the provisions of the Budapest Treaty and was assigned the ATCC accession number CRL 11965.

The production of a soluble murine LT-beta-R fusion molecule (mLT-beta-R-Fc) is described in Example 2 of U.S. Pat. No. 5,925,351 incorporated by reference herein. A CHO line made according to Example 2 of U.S. Pat. No. 5,925,351 that secretes mLT-beta-R-Fc is called "mLT beta; R-hG1 CHO#1.3.BB". A sample of this line was deposited on Jul. 21, 1995 with the American Type Culture Collection (ATCC) (Rockville, Md.) according to the provisions of the Budapest Treaty and was assigned the ATCC accession number CRL 11964.

Different amino acid residues forming the junction point of the receptor-Ig fusion protein may alter the structure, stability and ultimate biological activity of the soluble LT-beta receptor fusion protein. One or more amino acids may be added to the C-terminus of the selected LT-beta-R fragment to modify the junction point with the selected fusion domain.

The N-terminus of the LT-beta-R fusion protein may also be varied by changing the position at which the selected LT-beta-R DNA fragment is cleaved at its 5' end for insertion into the recombinant expression vector. The stability and activity of each LT-beta-R fusion protein may be tested and optimized using routine experimentation and the assays for selecting LT-beta-R blocking agents described herein.

Using the LT-beta-R ligand binding domain sequences within the extracellular domain shown in FIG. 1, amino acid sequence variants may also be constructed to modify the affinity of the soluble LT-beta receptor or fusion protein for LT ligand. The soluble LT-beta-R molecules of this invention can compete for surface LT ligand binding with endogenous cell surface LT-beta receptors. It is envisioned that any soluble molecule comprising a LT-beta-R ligand binding domain that can compete with cell surface LT-beta receptors for LT ligand binding is a LT-beta-R blocking agent that falls within the scope of the present invention.

In another embodiment of this invention, antibodies directed against the human LT-beta receptor (anti-LT-beta-R Abs) function as LT-beta-R blocking agents for use in treating conditions that place individuals, including human, in, or at risk of, viral-induced systemic shock and respiratory distress. The anti-LT-beta-R Abs of this invention can be polyclonal or monoclonal (mAbs) and can be modified to optimize their ability to block LT-beta-R signalling, their in vivo bioavailability, stability, or other desired traits.

Polyclonal antibody sera directed against the human LT-beta receptor are prepared using conventional techniques by injecting animals such as goats, rabbits, rats, hamsters or mice subcutaneously with a human LT-beta receptor-Fc fusion protein (Example 1 of U.S. Pat. No. 5,925,351) in complete Freund's adjuvant, followed by booster intraperitoneal or subcutaneous injection in incomplete Freund's. Polyclonal antisera containing the desired antibodies directed against the LT-beta receptor are screened by conventional immunological procedures.

Mouse monoclonal antibodies (mAbs) directed against a human LT-beta receptor-Fc fusion protein are prepared as described in U.S. Pat. No. 5,925,351, Example 5. A hybridoma cell line (BD.A8.AB9) which produces the mouse anti-human LT-beta-R mAb BDA8 was deposited on Jan. 12, 1995 with the American Type Culture Collection (ATCC) (10801 University Boulevard, Manassas, Va. 20110-2209) according to the provisions of the Budapest Treaty, and was assigned the ATCC accession number HB11798.

Various forms of anti-LT-beta-R antibodies can also be made using standard recombinant DNA techniques (Winter and Milstein, Nature, 349, pp. 293-99 (1991)). For example, "chimeric" antibodies can be constructed in which the antigen binding domain from an animal antibody is linked to a human constant domain (e.g. Cabilly et al., U.S. Pat. No. 4,816,567; Morrison et al., Proc. Natl. Acad. Sci. U.S.A., 81, pp. 6851-55 (1984)). Chimeric antibodies reduce the observed immunogenic responses elicited by animal antibodies when used in human clinical treatments. In addition, recombinant "humanized antibodies" which recognize the LT-beta-R can be synthesized. Humanized antibodies are chimeras comprising mostly human IgG sequences into which the regions responsible for specific antigen-binding have been inserted (e.g. WO 94/04679). Animals are immunized with the desired antigen, the corresponding antibodies are isolated, and the portion of the variable region sequences responsible for specific antigen binding are removed. The animal-derived antigen binding regions are then cloned into the appropriate position of human antibody genes in which the antigen binding regions have been deleted. Humanized antibodies minimize the use of heterologous (inter-species) sequences in human antibodies, and are less likely to elicit immune responses in the treated subject.

Construction of different classes of recombinant anti-LT-beta-R antibodies can also be accomplished by making chimeric or humanized antibodies comprising the anti-LT-beta-R variable domains and human constant domains (CH1, CH2, CH3) isolated from different classes of immunoglobulins. For example, anti-LT-beta-R IgM antibodies with increased antigen binding site valencies can be recombinantly produced by cloning the antigen binding site into vectors carrying the human mu chain constant regions (Arulanandam et al., J. Exp. Med., 177, pp. 1439-50 (1993); Lane et al., Eur. J. Immunol., 22, pp. 2573-78 (1993); Traunecker et al., Nature, 339, pp. 68-70 (1989)). In addition, standard recombinant DNA techniques can be used to alter the binding affinities of recombinant antibodies with their antigens by altering amino acid residues in the vicinity of the antigen binding sites. The antigen binding affinity of a humanized antibody can be increased by mutagenesis based on molecular modeling (Queen et al., Proc. Natl. Acad. Sci. U.S.A., 86, pp. 10029-33 (1989); WO 94/04679).

It may be desirable to increase or to decrease the affinity of anti-LT-beta-R Abs for the LT-beta-R depending on the targeted tissue type or the particular treatment schedule envisioned. For example, it may be advantageous to treat a patient with constant levels of anti-LT-beta-R Abs with reduced ability to signal through the LT-beta pathway for semi-prophylactic treatments. Likewise, inhibitory anti-LT-beta-R Abs with increased affinity for the LT-beta-R may be advantageous for short-term treatments.

By testing other antibodies directed against the human LT-beta receptor, it is expected that additional anti-LT-beta-R antibodies that function as LT-beta-R blocking agents in humans can be identified for treating conditions that place individuals, including human, in, or at risk of, viral-induced systemic shock and respiratory distress using routine experimentation and the assays described herein.

Another preferred embodiment of this invention involves compositions and methods which comprise antibodies directed against LT ligand that function as LT-beta-R blocking agents. As described above for the anti-LT-beta-R Abs, anti-LT ligand antibodies that function as LT-beta-R blocking agents can be polyclonal or monoclonal, and can be modified according to routine procedures to modulate their antigen binding properties and their immunogenicity. The anti-LT antibodies of this invention can be raised against either one of the two LT subunits individually, including soluble, mutant, altered and chimeric forms of the LT subunit. If LT subunits are used as the antigen, preferably they are LT-beta subunits. If LT-alpha subunits are used, it is preferred that the resulting anti-LT-alpha antibodies bind to surface LT ligand and do not cross-react with secreted LT-alpha or modulate TNF-R activity (according to the assays described in Example 3 of U.S. Pat. No. 5,925,351).

Alternatively, antibodies directed against a homomeric (LT-beta) or a heteromeric (LT-alpha/62) complex comprising one or more LT subunits can be raised and screened for activity as LT-beta-R blocking agents. Preferably, LT-alpha 1/beta 2 complexes are used as the antigen. As discussed above, it is preferred that the resulting anti-LT-alpha 1/beta 2 antibodies bind to surfaceLT ligand without binding to secreted LT-alpha and without affecting TNF-R activity.

The production of polyclonal anti-human LT-alpha antibodies is described in applicants' co-pending application (WO 94/13808). Monoclonal anti-LT-alpha and anti-LT-beta antibodies have also been described (Browning et al., J. Immunol., 54, pp. 33-46 (1995)). Mouse anti-human LT-beta mAbs were prepared as described in Example 6 of U.S. Pat. No. 5,925,351. Hybridoma cell line (B9.C9.1) which produces the mouse anti-human LT-beta-R mAb B9 was deposited on Jul. 21, 1995 with the American Type Culture Collection (ATCC) (10801 University Boulevard, Manassas, Va. 20110-2209) according to the provisions of the Budapest Treaty, and was assigned the ATCC accession number 11962.

Monoclonal hamster anti-mouse LT-alpha/62 antibodies were prepared as described in Example 7 of U.S. Pat. No. 5,925,351. A hybridoma cell line (BB.F6.1) which produces the hamster anti-mouse LT-alpha/62 mAb BB.F6 was deposited on Jul. 21, 1995 with the American Type Culture Collection (ATCC) (10801 University Boulevard, Manassas, Va. 20110-2209) according to the provisions of the Budapest Treaty, and was assigned the ATCC accession number MB 11963.

A fluorescence-activated cell sorting (FACS) assay was developed to screen for antibodies directed against LT subunits and LT complexes that can act as LT-beta-R blocking agents as described in Examples 6 and 7 of U.S. Pat. No. 5,925,351. In this assay, soluble human LT-beta-R-Fc fusion protein is added to PMA-activated II-23 cells—which express surface LT complexes (Browning et al., J. Immunol., 154, pp. 33-46 (1995))—in the presence of increasing amounts of the test antibody. An antibody that can inhibit LT-beta receptor-ligand interaction by at least 20% is selected as a LT-beta-R blocking agent.

Using a LT-alpha/beta complex rather than a LT subunit as an antigen to immunize an animal may lead to more efficient immunization, or may result in antibodies having higher affinities for surface LT ligand. It is conceivable that by immunizing with the LT-alpha/62 complex, antibodies which recognize amino acid residues on both the LT-alpha and the LT-beta subunits (e.g., residues that form an LT-alpha/62 cleft) can be isolated. By testing antibodies directed against human LT-alpha/62 heteromeric complexes, it is expected that additional anti-LT antibodies that function as LT-beta-R blocking agents in humans can be identified using routine experimentation and the assays described herein.

Administration

The compositions described herein will be administered at an effective dose in methods for treating viral-induced systemic shock and respiratory distress in an individual. Determination of a preferred pharmaceutical formulation and a therapeutically efficient dose regiment for a given application is well within the skill of the art taking intoconsideration, for example, the condition and weight of the patient, the extent of desired treatment and the tolerance of the patient for the treatment. Doses of about 1 mg/kg of a soluble LT-beta-R are expected to be suitable starting points for optimizing treatment doses.

Determination of a therapeutically effective dose can also be assessed by performing in vitro experiments that measure the concentration of the LT-beta-R blocking agent required to coat target cells (LT-beta-R or LT ligand-positive cells depending on the blocking agent) for 1 to 14 days. The receptor-ligand binding assays described herein can be used to monitor the cell coating reaction. LT-beta-R or LT ligand-positive cells can be separated from activated lymphocyte populations using FACS. Based on the results of these in vitro binding assays, a range of suitable LT-beta-R blocking agent concentrations can be selected to test in animals according to the assays described herein.

Administration of the soluble LT-beta-R molecules, anti-LT ligand and anti-LT-beta-R Abs of this invention, alone or in combination, including isolated and purified forms of the antibodies or complexes, their salts or pharmaceutically acceptable derivatives thereof, may be accomplished using any of the conventionally accepted modes of administration of agents which exhibit immunosuppressive activity.

The pharmaceutical compositions used in these therapies may also be in a variety of forms. These include, for example, solid, semi-solid and liquid dosage forms such as tablets, pills, powders, liquid solutions or suspensions, suppositories, and injectable and infusible solutions. The preferred form depends on the intended mode of administration and therapeutic application.

Modes of administration may include oral, parenteral, subcutaneous, intravenous, intralesional or topical administration. The soluble LT-beta-R molecules, anti-LT ligand and anti-LT-beta-R Abs of this invention may, for example, be placed into sterile, isotonic formulations with or without cofactors which stimulate uptake or stability. The formulation is preferably liquid, or may be lyophilized powder. For example, the soluble LT-beta-R molecules, anti-LT ligand and anti-LT-beta-R Abs of this invention may be diluted with a formulation buffer comprising 5.0 mg/ml citric acid monohydrate, 2.7 mg/ml trisodium citrate, 41 mg/ml mannitol, 1 mg/ml glycine and 1 mg/ml polysorbate 20. This solution can be lyophilized, stored under refrigeration and reconstituted prior to administration with sterile Water-For-Injection (USP).

The compositions also will preferably include conventional pharmaceutically acceptable carriers well known in the art (see for example Remington's Pharmaceutical Sciences, 16th Edition, 1980, Mac Publishing Company). Such pharmaceutically acceptable carriers may include other medicinal agents, carriers, genetic carriers, adjuvants, excipients, etc., such as human serum albumin or plasma preparations. The compositions are preferably in the form of a unit dose and will usually be administered one or more times a day.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained releasecarriers include semipermeable polymer matrices in the form of shaped articles such as suppositories or microcapsules. Implantable or microcapsular sustained release matrices include polylactides (U.S. Pat. No. 3,773, 319; EP 58,481), copolymers of L-glutamic acid and ethyl-L-glutamate (Sidman et al., Biopolymers, 22, pp. 547-56 (1985)); poly(2-hydroxyethyl-methacrylate) or ethylene vinyl acetate (Langer et al., J. Biomed. Mater. Res., 15, pp. 167-277 (1981); Langer, Chem. Tech., 12, pp. 98-105 (1982)).

Liposomes containing soluble LT-beta-R molecules, anti-LT ligand and anti-LT-beta-R Abs of this invention, alone or in combination, can be prepared by well-known methods (See, e.g. DE 3,218,121; Epstein et al., Proc. Natl. Acad. Sci. U.S.A., 82, pp. 3688-92 (1985); Hwang et al., Proc. Natl. Acad. Sci. U.S.A., 77, pp. 4030-34 (1980); U.S. Pat. Nos. 4,485,045 and 4,544,545). Ordinarily the liposomes are of the small (about 200-800 Angstroms) unilamellar type in which the lipid content is greater than about 30 mol. % cholesterol. The proportion of cholesterol is selected to control the optimal rate of soluble LT-beta-R molecule, anti-LT ligand and anti-LT-beta-R Ab release.

The soluble LT-beta-R molecules, anti-LT ligand and anti-LT-beta-R Abs of this invention may also be attached to liposomes containing other LT-beta-R blocking agents, immunosuppressive agents or cytokines to modulate the LT-beta-R blocking activity. Attachment of LT-beta-R molecules, anti-LT ligand and anti-LT-beta-R Abs to liposomes may be accomplished by any known cross-linking agent such as heterobifunctional cross-linking agents that have been widely used to couple toxins or chemotherapeutic agents to antibodies for targeted delivery.conjugation to liposomes can also be accomplished using the carbohydrate-directed cross-linking reagent 4-(4-maleimidophenyl) butyric acid hydrazide (MPBH) (Duzgunes et al., J. Cell. Biochem. Abst. Suppl. 16E 77 (1992)).

The LT-beta-R blocking agents of the compositions and methods of this invention can be modified to obtain a desirable level of LT-beta-R signalling depending on the condition, disorder or disease being treated. It is envisioned that the absolute level of LT-beta-R signalling can be fine-tuned by manipulating the concentration and the affinities of the LT-beta-R blocking agents for their respective molecular targets. For example, in one embodiment of this invention, compositions comprising soluble LT-beta-R molecules are administered to a subject. The soluble LT-beta receptor can effectively compete with cell surface LT-beta receptors for binding surface LT ligands. The ability to compete with surface LT ligands depends on the relative concentrations of the soluble and the cell surface LT-beta-R molecules, and on their relative affinities for ligand binding.

Soluble LT-beta-R molecules harboring mutations that increase or decrease the binding affinity of that mutant soluble LT-beta-R with surface LT ligand can be made using standard recombinant DNA techniques well known to those of skill in the art. Large numbers of molecules with site-directed or random mutations can be tested for their ability to act as LT-beta-R blocking agents using routine experimentation and the techniques described herein. Similarly, in another embodiment of this invention, antibodies directed against either the LT-beta receptor or one or more of the LT ligand subunits function as LT-beta-R blocking agents. The ability for these antibodies to block LT-beta receptor signalling can be modified by mutation, chemical modification or by other methods that can vary the effective concentration or activity of the antibody delivered to the subject.

Uses

As a general matter, the methods of the present invention may be utilized for inducing an antiviral response in an individual comprising administering to the individual an effective amount of a LT-B blocking agent and a pharmaceutically acceptable carrier. The viral response to be treated may be caused by any number of known viruses, including but not limited to Sin Nombre (SNV), Ebola, Marburg, Lassa, and Dengue.

Equivalents

The invention may be embodied in other specific forms without departing from the spirit or essential characteristics thereof. The foregoing embodiments are therefore to be considered in all respects illustrative of, rather than limiting on, the invention disclosed herein. Scope of the invention thus is indicated by the appended claims rather than by the foregoing description, and all changes which come within the meaning and range of equivalency of the claims are intended to be embraced therein.

Example

Tumor necrosis factor (TNF α) plays a key role in facilitating acute shock responses to viral infections and other immunogens (K. C. F. Sheehan, N. H. Ruddle, and R. D. Schreiber., *J. Immunol.*, 142, 3884 (1989); G. W. H. Wong and D. V. Goeddel *Nature* 323, 819 (1986); B. Beutler, I. W. Milsark, A. Cerami, *Science* 229, 869 (1985); F. Mackay, P. R. Bourdon, D. A. Griffiths, et al. *J. Immunol.* 159, 3299 (1997); P. D. Crowe, T. L. VanArsdale, B. N. Walter, et al. *Science*

Figure 3:
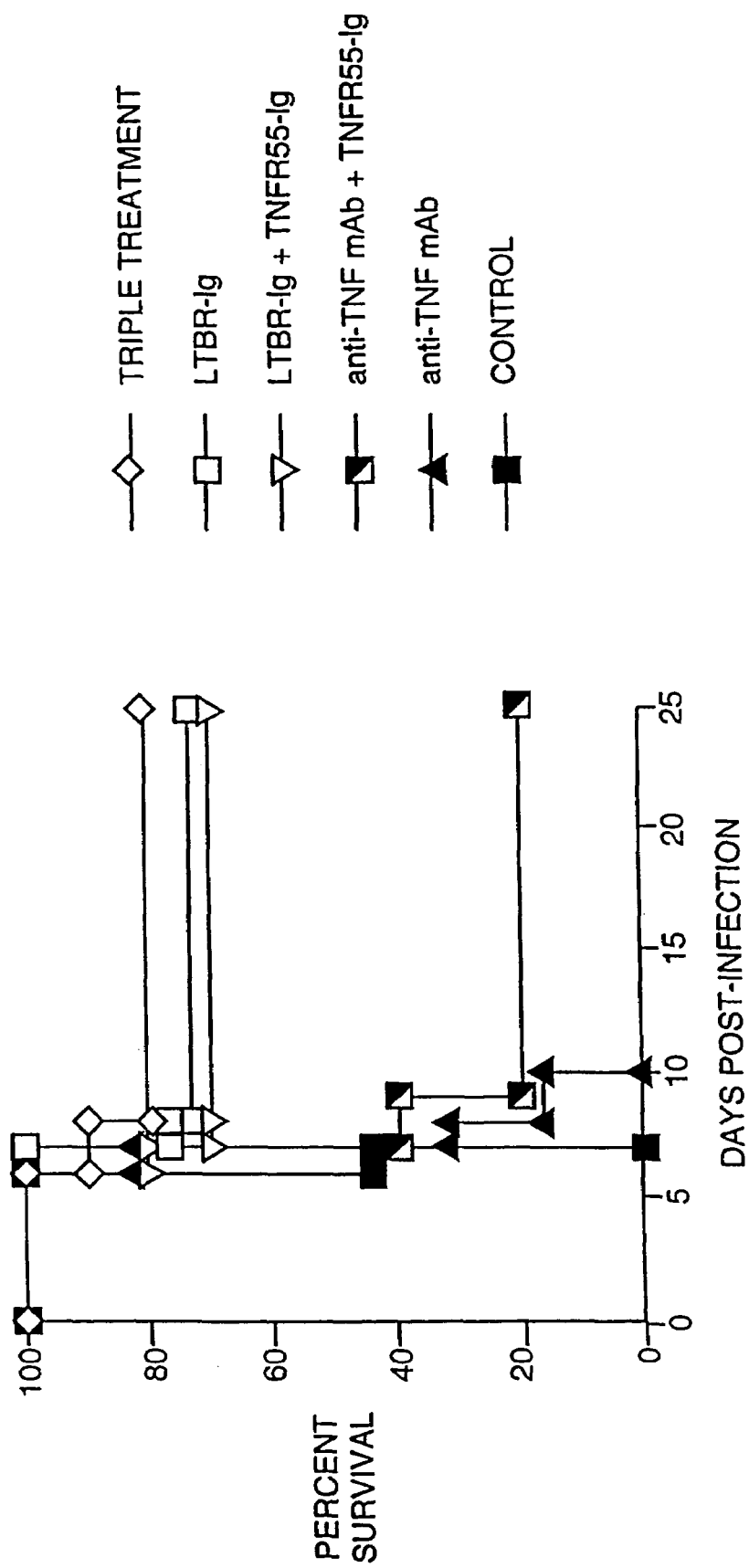
FIG. 3 shows that blockage of the LTβR signaling pathways significantly improves survival rates among Clone 13 infected NZB mice. Mortality curves for Clone 13 infected NZB mice treated as described are presented here. NZB mice were given $2.5 \times 10^6$ pfu Cl 13 i.v. followed by two i.p. injections containing 250 µg of TN3-19.12 antibody in endotoxin free PBS (see reference S) on days 1 and day 4 post-infection. Control mice were injected with the same volume of PBS lacking antibody on the same days. Mice were treated as described in reference R. For the triple treated group, TNFR55-Ig and LTβR-Ig proteins were given on day 0 and day 3 post-infection, i.p., in 200 µg amounts. Control mice were given human antibody used in the synthesis of these fusion proteins (AY1943-29) on the same days in identical amounts. Mice receiving LTβR-Ig only were treated identically, except the TNFR55-Ig injections were omitted. Data was compiled from several experiments anti-TNF (TN3-19.12) alone, n=16 for LTβR-Ig alone, n=10 for the triple treatment group, (n=10 for the triple treatment group, n=22 for LTβR-Ig alone, n=10 for the LTβR-Ig+TNFR55-Ig group, n=5 for the anti-TNF and TNFR55-Ig treated group, n=6 for anti-TNF (TN3-19.12) alone, and n=25 for Control).

264, 707 (1994)). During episodes of Dengue Fever involving shock, levels of TNFα in sera from patients are elevated as are levels of soluble TNFR-75 (D. Hober, et al., *J. Trop. Med. Hyg.*, 48, 324 (1993); D. B. Bethell, K. Flobbe, C. X. T. Phuong, et al., *J. Infect. Dis.*, 177, 778 (1998)). We measured TNFα levels in the sera of mice infected with a variant of lymphocytic choriomeningitis virus, LCMV, Clone 13 (LCMV-13) (HH, II). TNFα levels in the sera of mice infected with LCMV-13 were found to be just above the level of detection for the assay until day 4 post infection (Serum TNFα levels were measured by ELISA assay (Genzyme Corporation, catalog number 80-2802-00)). On days 5 and 6, when the disease is at its peak, soluble TNFα levels in the serum increased 3-6 fold above normal (data not shown). We therefore chose to block TNFα function by using a monoclonal antibody, TN3-19.12, which is known to bind both secreted TNFα, thus causing its depletion from the mouse as verified by ELISA (K. C. F. Sheehan, N. H. Ruddle, and R. D. Schreiber., *J. Immunol.*, 142, 3884 (1989) G. W. H. Wong and D. V. Goeddel *Nature* 323, 819 (1986); B. Beutler, I. W. Milsark, A. Cerami, *Science* 229, 869 (1985); F. Mackay, P. R. Bourdon, D. A. Griffiths, et al. *J. Immunol.* 159, 3299 (1997); P. D. Crowe, T. L. VanArsdale, B. N. Walter, et al. *Science* 264, 707 (1994); D. Hober, et al., *J. Trop. Med. Hyg.*, 48, 324 (1993); D. B. Bethell, K. Flobbe, C. X. T. Phuong, et al., *J. Infect. Dis.*, 177, 778 (1998)). Serum TNFα levels were measured by ELISA assay (Genzyme Corporation, catalog number 80-2802-00). NZB mice were given $2.5 \times 10^6$ pfu Cl 13 i.v. followed by two i.p. injections containing 250 µg of TN3-19.12 antibody in endotoxin free PBS (see reference S) on days 1 and day 4 post-infection. Control mice were injected with the same volume of PBS lacking antibody on the same days. This treatment (anti-TNF) had little effect on the survival rate of these mice (FIG. 3). Lymphotoxin alpha (LTα), also known as TNFβ, though it shares identical receptors and many of its biological effects with TNFα, is not recognized by this antibody (F. Mackay, P. R. Bourdon, D. A. Griffiths, et al. *J. Immunol.* 159, 3299 (1997). It is possible that targeting both TNFα and LTα are required to increase survival rates. To test this hypothesis, we used the above TN3-19.12 mAb and a receptor fusion protein that fused the extracellular domain of the TNF p55 receptor to CH2 and CH3 domains of human IgG1 (TNFR55-Ig)(W. R. Force, B. N. Walter, C. Hession, et. al., *J. Immunol.*, 155, 5280 (1995); G. T. Miller, P. S. Hochman, W. Meier, et. al., *JEM.*, 178, 211 (1993); J. L. Browning, I. Dougas, A. Ngam-ek, et al., *J. Immunol.*, 154:33 (1995). Mice were treated as described in reference R. For the triple treated group, TNFR55-Ig and LTβR-Ig proteins were given on day 0 and day 3 post-infection, i.p., in 200 µg amounts. Control mice were given human antibody used in the synthesis of these fusion proteins (AY1943-29) on the same days in identical amounts. Mice receiving LTβR-Ig only were treated identically, except the TNFR55-Ig injections were omitted). This treatment also did not significantly alter survival rates in LCMV-13 infected NZB mice (See anti-TNF and TNFR55-Ig group). The membrane form of lymphotoxin, a heteromer of LTα and LTβ, does not recognize TNFR-75 or TNFR-55 but rather binds to a third receptor called LTβR (15). We elected to use a fusion protein containing the LTβR extracellular domain also attached to CH2 and CH3 domains of human IgG1 (LTβR-Ig). Treatment of the mice with anti-TNFα mAb, TNFR55-Ig and LTβR-Ig (triple treatment or TNFR55-IG and LTβR-Ig) resulted in a dramatic increase in survival, to 80% and 70% respectively. In contrast, only 20% of mice treated with anti-TNFα mAb and TNFR55-Ig survived infection. Recently a second ligand for LTβR, LIGHT, was identified (D. N. Mauri, R. Ebner, R. I. Montgomery, et al. *Immunity* 8, 21 (1998); R. I. Montgomery, M. S. Warner, B. Lum, et al. *Cell* 87, 427 (1996)). LIGHT has also been shown to bind the herpesvirus entry mediator (HVEM), a type I transmembrane protein with significant homology to members of the TNFR family that is expressed on activated CD4 and CD8 T cells (D. N. Mauri, R. Ebner, R. I. Montgomery, et al. *Immunity* 8, 21 (1998); R. I. Montgomery, M. S. Warner, B. Lum, et al. *Cell* 87, 427 (1996)). Based on results presented here, prevention of LTβR signaling and potentially HVEM signaling by the binding of $LT\beta_2\alpha_1$ and LIGHT by LTβR-Ig was likely responsible for most of the effect seen in the triple treatment group. We affirmed this hypothesis by treating LCMV-13 infected NZB mice with just the LTβR-Ig fusion protein. The survival rate of mice in this group (73%) was almost as high as the triple treated group (FIG. 3). Taken together, these data represent the first demonstration that the LTβR and/or HVEM signaling pathway is involved in the orchestration of an acute lethal disease involving systemic shock and respiratory distress.

Figure 4:
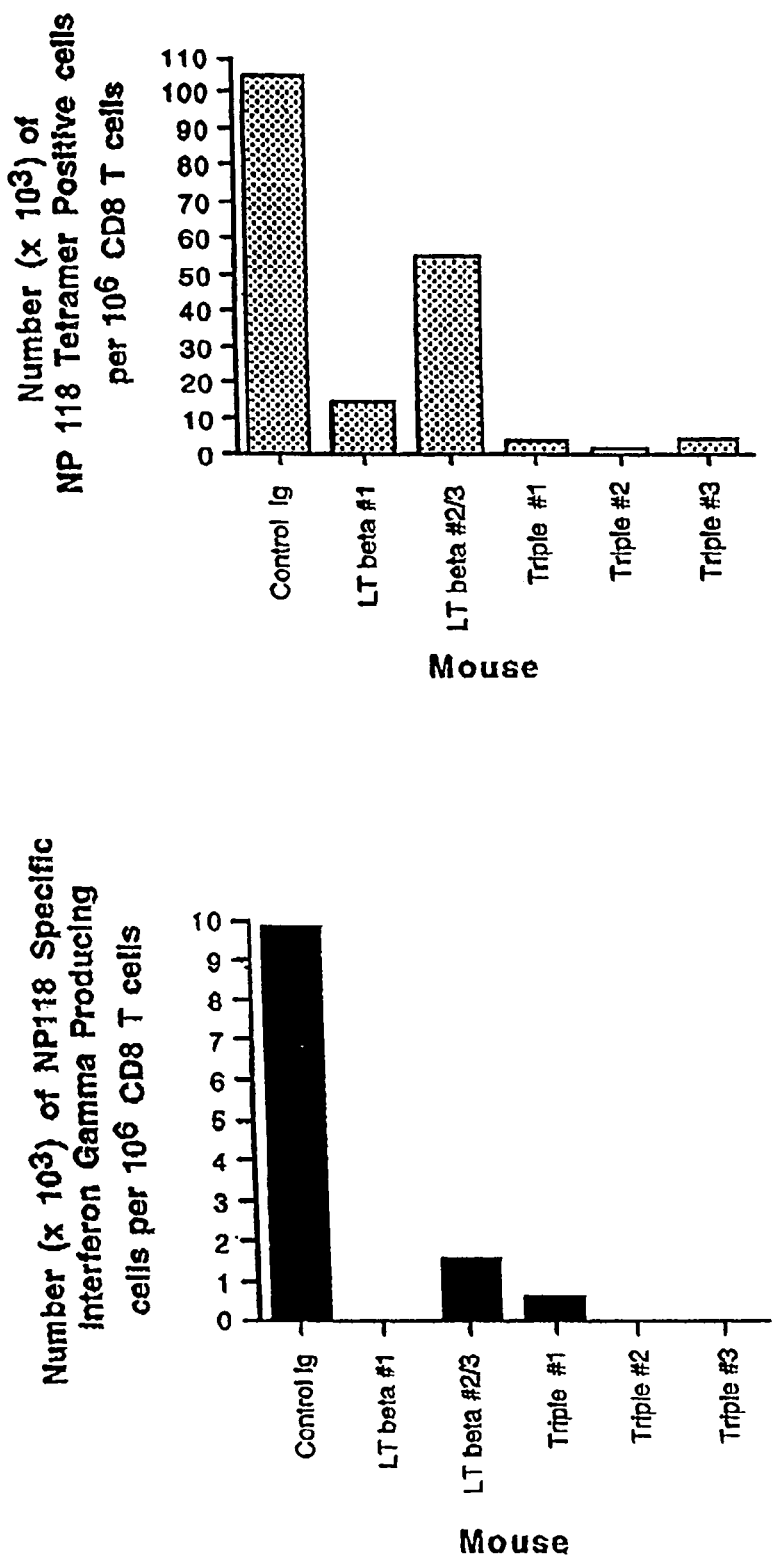
FIG. 4 shows that blockage of the LTβR pathway results in a decrease in CD8 T cell function. Splenocytes from mice in different treatment groups were harvested on day 6 post-infection and stained with an $L^d$ tetramer containing a NP118 9 mer peptide as previously described. Values given are adjusted for non-specific background staining. To monitor interferon gamma production in response to the same peptide, cells were incubated for 5 hours at 37° C. in the presence of NP118 at 0.1 µg/ml final concentration and IL-2. Values given here are adjusted for background levels in the absence of peptide. Spleenocytes from three mice treated with control human Ig were pooled as were those from two LTβR-Ig mice (LT beta #2/3). All other results are from individual mice.
Figure 5:
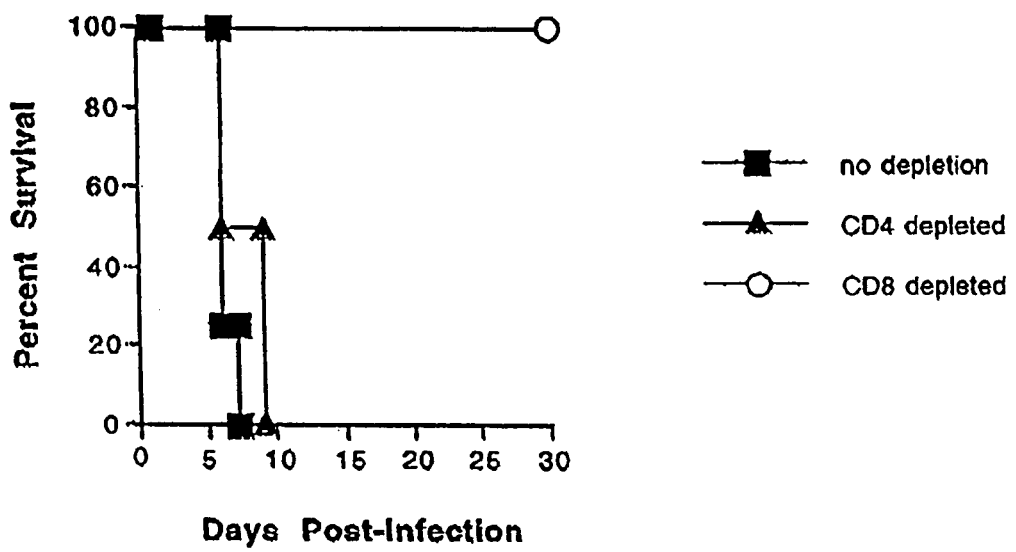
FIG. 5 shows that depletion of $CD8^+$ T cells, not $CD4^+$ T cells, reverses the lethal effects of LCMV-13 infection in NZB mice. Mice were treated as described for depletion of cell populations in vivo. A mortality curve is presented for each of the treated groups (n=4).

In an effort to determine the mechanism of survival behind LTβ blockage treatment, both CD8/tetramer co-staining for NP118 specific T cells, the dominant CD8 epitope in the NZB $L^D$ system, and intracellular staining for interferon gamma production by spleenocytes stimulated with NP118 peptide were performed on samples from LCMV-13 infected NZB mice who were treated with control antibody, LTβR-Ig alone, or triple treated; FIG. 4 demonstrates a reduction in the number of NP118 specific CD8 T cells with the greatest effect seen in the triple treatment mice. In mice treated with control antibody, only 10% of tetramer positive cells actively produced INFγ. The emergence of anergic T cells during LCMV-13 infection has been previously documented and is likely due to high levels of viral antigen in the mouse (FIG. 1). Not only has the number of NP118 specific cells declined in the LTβR-Ig treated mice, but the percentage of those cells producing INFγ was also reduced. This effect was even more pronounced in the triple treatment group. Thus it is possible that the CD8 compartment may be the source of this lethal NZB response to LCMV-13 infection. The fact that activated CD8s are known to display $LT\beta_2\alpha_1$ is consistent with this hypothesis (Y. Abe, A. Horiuchi, Y. Osuka, et al., *Lymph. Ctyok. Res.*, 11, 115 (1992); C. F. Ware, P. D. Crowe, M. H. Grayson, et al., *J. Immunol.*, 149, 3881 (1992); J. L. Browning, A. Ngam-ek, P. Lawton, et al., *Cell*, 72, 847 (1993)). To support this assertion, we depleted infected NZB mice of their CD8 or CD4 positive T cells in vivo (Male NZB mice were given $2.5 \times 10^6$ pfu LCMV-13 i.v. followed by two 500 µl i.p. injections of anti T cell antibody. The mAb Lyt2.43 was used to deplete $CD8^+$ T cells while the GK1.5 (M1) antibody was used for $CD4^+$ T cell depletion. Both antibodies were prepared by an ammonium sulfate precipitation from hybridoma supernatants followed by dialysis against PBS. FACS analysis was used to verify the depletion in several of the mice.). Depletion of CD4 T cells did not increase survival. In contrast, depletion of CD8 T cells resulted in 100% survival in the absence of disease symptoms unlike the LTβR-Ig treated mice (FIG. 5). Because viral titers in several tissues of CD8 depleted mice were higher than those not treated, it is likely that death resulted from a toxic immune response mediated by CD8 T cells rather than from destruction of tissues by viral infection.

We have reported here that NZB mice when infected with a high dose of LCMV-13 intravenously develop an acute, rapidly progressive disease that shares several common traits with Ebola, Marburg, Lassa, Dengue, and Sin Nombre infections. Lethality of this illness was dependent on the presence of $CD8^+$T cells which are known to express TNFα, LTα, and LTβ when activated. Though this is an encouraging finding, treatment of viral infection by depletion of CD8+T cells would not be advisable. Such treatment could leave patients vulnerable to other opportunistic infections. Furthermore, since viral clearance is unlikely in the absence of CTLs the risk of the patient tolerizing to the virus upon re-establishment of the CD8+ compartment is very real. We have shown that blockage of the LTβR/HVEM pathways by administration of LTβR-Ig represents a powerful treatment that is transient in nature, with rapid recovery to homeostasis once treatment is stopped (Mackay and Browning, unpublished). Surviving mice treated in this manner eventually cleared virus from tissues tested (data not shown) and no longer show signs of disease.

These data represent the first demonstration that LTβR signaling plays an important role in antiviral responses and CD8 T cell function. The lymphotoxin system is intimately linked to organization of lymphoid architecture most likely via control of the expression of several chemokines that direct T and B cell organization (. Chaplin et al. *Curr. Opin. Immunol.* 10, 289 (1998), J. Cyster, in press). The mature functional status of follicular dendritic cells is maintained by constant B cell signaling and these cells disappear within one day upon cessation of the LTβR signaling. These cells are critical for the presentation of antigen to the B and T cell compartments. A reasonable speculation is that some aspect of antigen presentation to CD8 cells or the proper positioning of these cells in a chemokine gradient during maturation is prevented by disruption of LTβR signaling. Previous studies of LT function have focused primarily on B cell biology and the involvement in a T cell function was unforeseen. Either LT has additional functions or these data reflect a role for the novel ligand LIGHT. What role HVEM and LIGHT may play in the progression of the disease documented here is unclear at present.

What is claimed is:

1. A method of inducing an antiviral response or treating a viral infection in an individual suffering from viral-induced systemic shock mediated by CD8 T cells and/or viral-induced pulmonary distress mediated by CD8 T cells, comprising administering to the individual an effective amount of a pharmaceutical composition comprising a lymphotoxin-beta (LT-beta) or lymphotoxin-beta receptor (LT-beta-R) blocking agent selected from the group consisting of an antibody directed against LT-beta, a soluble LT-beta-R, an antibody directed against LT-beta-R, and an antibody directed against surface LT ligand, and a pharmaceutically acceptable carrier, such that an antiviral response is induced or viral infection treatment occurs.

2. The method of claim 1, wherein the composition comprises a soluble LT-beta-R or an anti-LT-beta-R antibody which binds LT-beta-R.

3. A method of treating viral-induced systemic shock mediated by CD8 T cells in an individual comprising administering to the individual an effective amount of a pharmaceutical composition comprising a lymphotoxin-beta (LT-beta) or lymphotoxin-beta receptor (LT-beta-R) blocking agent selected from the group consisting of a an antibody directed against LT-beta, a soluble LT-beta-R, an antibody directed against LT-beta-R, and an antibody directed against surface LT ligand, and a pharmaceutically acceptable carrier, such that viral-induced systemic shock is treated.

4. The method of claim 3, wherein the composition comprises a soluble LT-beta-R or an anti-LT-beta-R antibody which binds LT-beta-R.

5. A method of treating viral-induced pulmonary distress mediated by CD8 T cells in an individual comprising administering to the individual an effective amount of a pharmaceutical composition comprising a lymphotoxin-beta (LT-beta) or lymphotoxin-beta receptor (LT-beta-R) blocking agent selected from the group consisting of an antibody directed against LT-beta, a soluble LT-beta-R, an antibody directed against LT-beta-R, and an antibody directed against surface LT ligand, and a pharmaceutically acceptable carrier, such that viral-induced pulmonary distress is treated.

6. The method of claim 5, wherein the composition comprises a soluble LT-beta-R or an anti-LT-beta-R antibody which binds LT-beta-R.

7. The method of any of claims 2, 4 or 6, wherein the soluble LT-beta-R comprises a LT-beta-R/immunoglobulin fusion (Ig fusion) protein.

8. The method of any of claims 1, 3 or 5 wherein the soluble LT-beta-R comprises a ligand binding domain that can selectively bind to surface LT ligand.

9. The method of any of claims 1, 2, 3, 4, 5 or 6, wherein said individual is infected with Sin Nombre Virus, Marburg virus, Lassa virus, or Dengue virus.

10. The method of any of claims 1, 3 or 5, wherein the soluble LT-beta-R comprises a soluble human LT-beta-R.

11. The method of claim 10, wherein the soluble human LT-beta-R is fused to one or more heterologous protein domains.

12. The method of claim 11, wherein the heterologous protein domain is selected from the group consisting of immunoglobulins, serum albumin, lipoproteins, apolipoproteins and transferrin.

13. The method of claim 11, wherein the heterologous protein domain comprises a human immunglobulin Fc domain.

14. The method of claim 8, wherein the ligand binding domain comprises a functional fragment of soluble human LT-beta-R sequence encoding an LT-beta-R ligand binding domain.

15. A method of inducing an antiviral response in a human suffering from viral-induced systemic shock mediated by CD8 T cells and/or viral-induced pulmonary distress mediated by CD8 T cells, comprising administering to the human a pharmaceutical composition comprising a polypeptide that comprises a soluble ligand binding domain of human LT-beta-R fused to a human IgG Fc domain and a pharmaceutically acceptable carrier, such that an antiviral response is induced.

16. The method of claim 15, wherein the ligand binding domain comprises the sequence of the extracellular portion of human LT-beta-R.

17. The method of any of claim 15, wherein the ligand binding domain comprises an extracellular region of the human LT-beta-R sequence.

18. The method of any of claim 15, wherein the ligand binding domain consists essentially of the soluble human LT-beta-R sequence.

19. A method of inducing an antiviral response or treating viral infection in an individual infected with Sin Nombre Virus (SNV) who is suffering from viral-induced pulmonary distress, comprising administering to the individual an effective amount of a pharmaceutical composition comprising an LT-beta blocking agent comprising either an antibody directed against LT-beta or an antibody directed against surface LT ligand, and a pharmaceutically acceptable carrier, such that an antiviral response is induced or viral infection treatment occurs.

20. A method of inducing an antiviral response or treating viral infection in an individual infected with Sin Nombre Virus (SNV) who is suffering from viral-induced pulmonary distress, comprising administering to the individual an effective amount of a pharmaceutical composition comprising a soluble LT-beta-R, and a pharmaceutically acceptable carrier, such that an antiviral response is induced or viral infection treatment occurs.

21. A method of treating a viral infection in an individual infected with Sin Nombre Virus (SNV) who is suffering from viral-induced systemic shock, comprising administering to the individual an effective amount of a pharmaceutical composition comprising a soluble LT-beta-R, and a pharmaceutically acceptable carrier, such that viral infection treatment occurs.

22. The method of claim 20 or 21, wherein the soluble LT-beta-R is fused to one or more heterologous protein domains.

23. The method of claim 20, wherein the heterologous protein domain is a human immunglobulin Fc domain.

24. The method of claim 20 or 21, wherein the ligand binding domain comprises a functional fragment of soluble human LT-beta-R sequence encoding an LT-beta-R ligand binding domain.

25. The method of claim 20 or 21, wherein the soluble lymphotoxin-beta-R comprises a ligand binding domain that can selectively bind to surface LT ligand.

26. The method of claim 22, wherein the heterologous protein domain is selected from the group consisting of immunoglobulins, serum albumin, lipoproteins, apolipoproteins and transferrin.

27. The method of claim 8, wherein the ligand binding domain comprises the sequence of the extracellular portion of human LT-beta-R.

28. The method of claim 8, wherein the ligand binding domain comprises an extracellular region of the human LT-beta-R sequence.

* * * * *